United States Patent [19]

Jewell

[11] Patent Number: 4,561,290

[45] Date of Patent: Dec. 31, 1985

[54] FLOAT VALVE APPARATUS FOR SOIL PERCOLATION MEASUREMENTS

[76] Inventor: Daniel E. Jewell, c/o Bureau of Reclamation, Department of the Interior, 2800 Cottage Way, Sacramento, Calif. 95825

[21] Appl. No.: 676,375

[22] Filed: Nov. 29, 1984

[51] Int. Cl.⁴ .......................................... G01N 15/00
[52] U.S. Cl. .................................... 73/38; 73/73
[58] Field of Search ...................................... 73/73, 38

[56] References Cited

U.S. PATENT DOCUMENTS

| | | | |
|---|---|---|---|
| 3,892,126 | 7/1975 | Curtin | 73/38 |
| 3,926,143 | 12/1975 | Hothan | 73/73 X |
| 3,945,247 | 3/1976 | Anderson | 73/73 |
| 4,072,044 | 2/1978 | Farwell et al. | 73/38 |
| 4,099,406 | 7/1978 | Fulkerson | 73/73 |
| 4,182,157 | 1/1980 | Fink | 73/38 |
| 4,341,110 | 7/1982 | Block | 73/73 X |

*Primary Examiner*—Jerry W. Myracle
*Assistant Examiner*—Joseph W. Roskos
*Attorney, Agent, or Firm*—Thomas Zack; E. Philip Koltos

[57] ABSTRACT

A float valve assembly, integral with a water supply system, responds to changes in a predetermined water level inside a test bore to regulate water flow through the float valve into the bore to maintain this water level. The float valve assembly can be positioned at different depths below ground level by suspension at the lower end of a premarked flexible hose (16) hanging freely inside the test bore. The float valve housing (1) is open at its lower end (3), so that water around it in the test bore can raise the float (8) within to throttle the water flowing down through a reducer (13) at the end of the hose and directly above the float. After an initial transient stage, the water in the test bore percolates away from the bore through the soil around it at a steady rate, measured to obtain the steady state percolation rate at that site at the selected depth.

11 Claims, 3 Drawing Figures

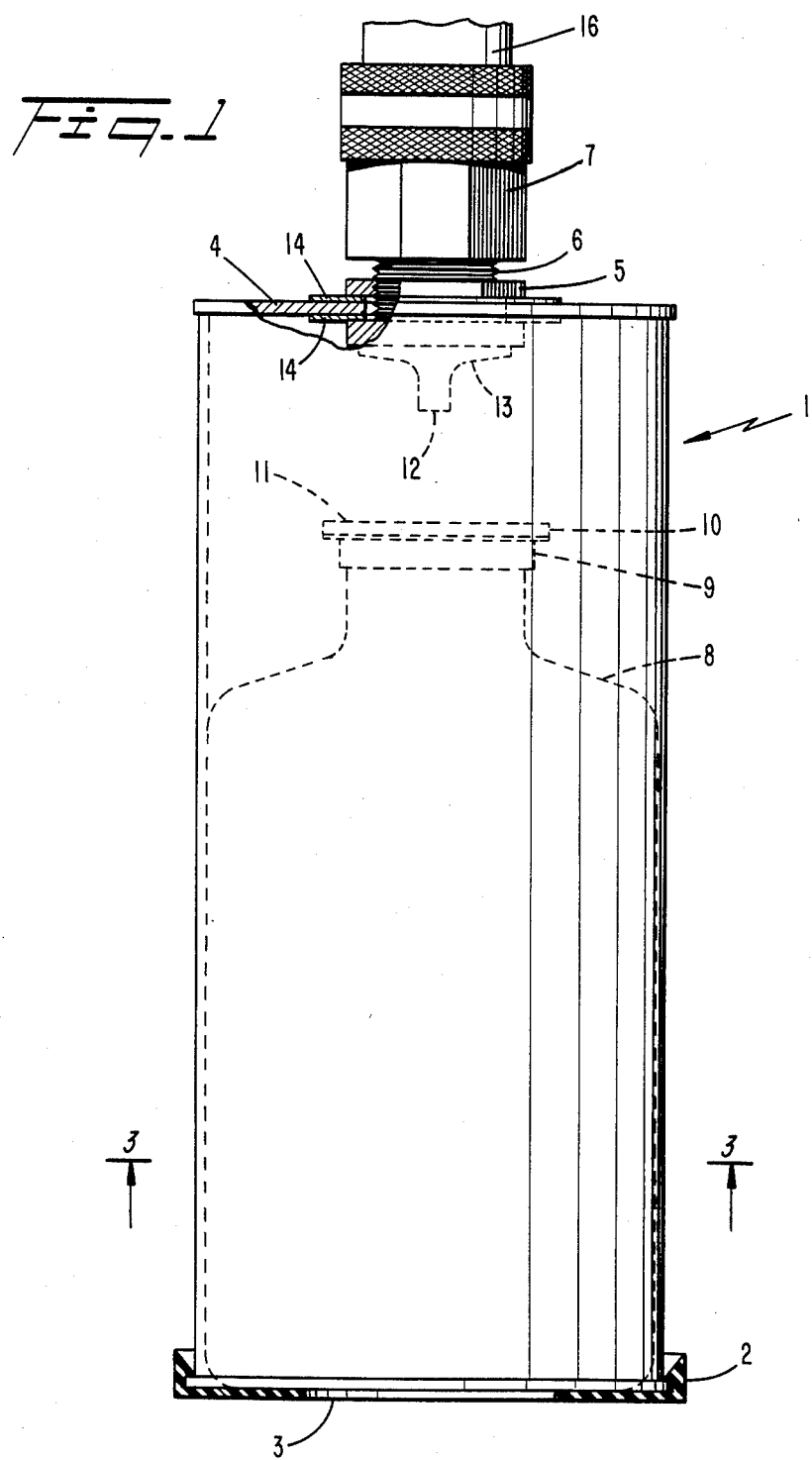

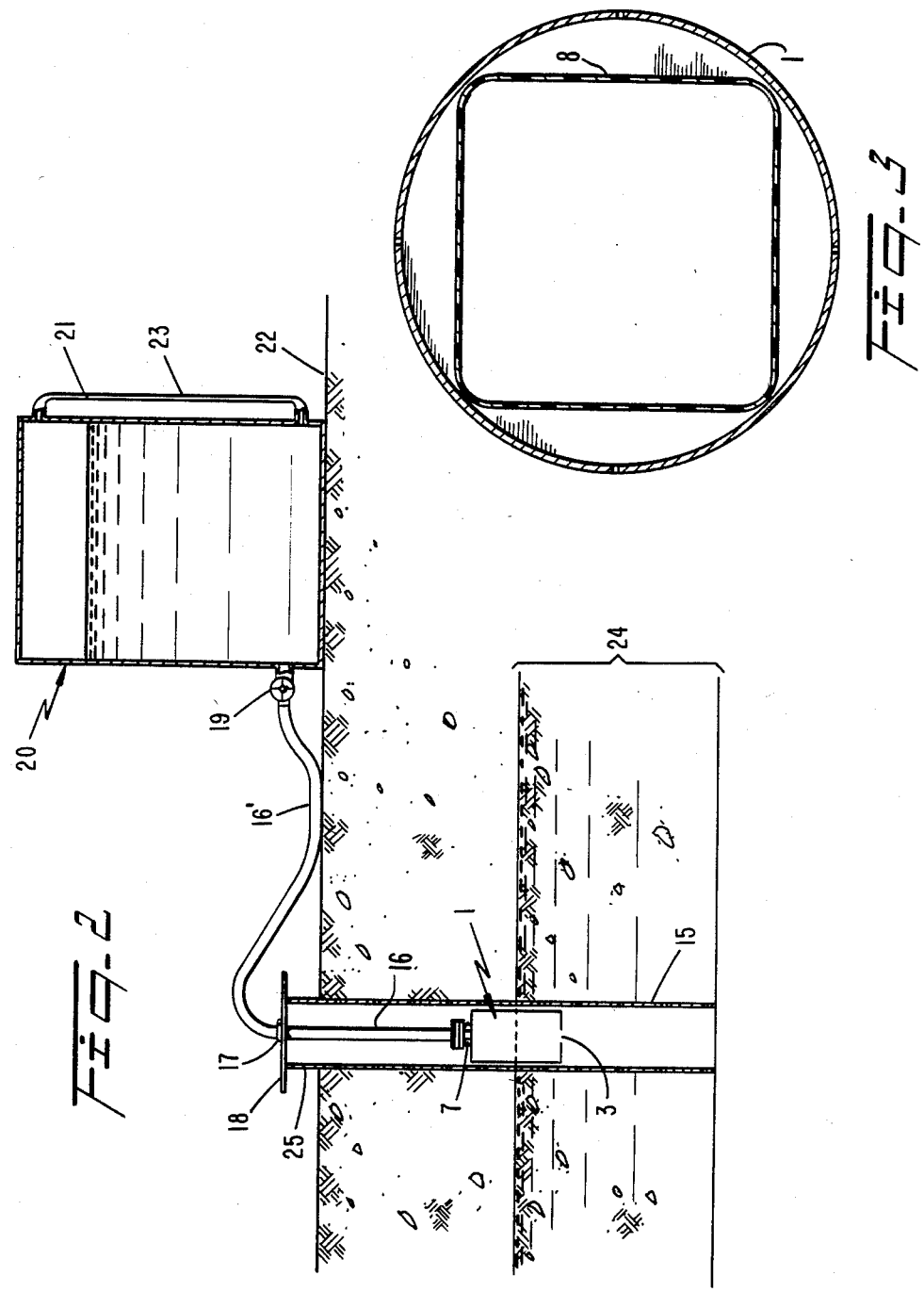

FLOAT VALVE APPARATUS FOR SOIL PERCOLATION MEASUREMENTS

TECHNICAL FIELD

This invention relates generally to an apparatus and a method for directly determining the rate at which water is physically conducted away through soil, i.e., the rate at which water percolates through the ground, at a test location, and more particularly toward an economical valve assembly for conducting shallow well pump-in tests to measure soil percolation.

BACKGROUND OF THE INVENTION

It is often very important to know what the permeabilities of soil are at a particular site, at various depths, in the absence of a water table. This information is useful, for example, in predicting the long-term irrigation suitability of farmlands. The primary interest here is in assessing the potential for detrimental water table formation. Once the soil's permeability is known, from such measurement of percolation rates at a site, it becomes possible to estimate the subsurface outflow capability for excess irrigation water (deep percolation) and, therefore, to predict the rate of water table buildup, if any. Internal drainage requirements, if needed, can also be assessed using this information.

Likewise, the ability of the ground to absorb and transmit water through the soil, as distinct from surface water run-off, is a very important factor to be considered in selecting the site of a building, factory, dam or any heavy stationary structure whose physical integrity and stability depend on the ability of the underlying soil to conduct away rainfall at a satisfactory rate. Determination of the ability of soil at a given construction site to so conduct away incident moisture provides assurance to an architect that there will be adequate support for the prospective structure. Such data may significantly affect both the design and its cost, as well as the willingness of local authorities to approve its construction.

A common practice is to drill or auger a circular hole a few inches in diameter to the depth of a few feet, then to pour water into the hole to an observed level and, thereafter, to observe the rate at which the water level drops in the test hole. Two recently issued patents on appartus for such purposes are U.S. Pat. No. 3,945,247 titled "Percolation Gauge," issued to Anderson on Mar. 23, 1976, and U.S. Pat. No. 4,182,157 titled "Soil Percolation Testing Apparatus" issued to Fink on Jan. 8, 1980. The Anderson apparatus has a hooked rod whose end is periodically moved to the water level in a test hole at recorded time intervals, thereby to provide data on the soil percolation rate. The Fink apparatus has a guided vertical rod supported by a float which drops in the test hole previously filled with water to hold up the float. In both these inventions, the user must determine both the fall of water level in a test hole as well as elapsed time, and then calculate the average percolation rate over that time through the soil at the test location. Neither invention teaches how to determine, directly, the rate at which water percolates through soil when the water level at a test site is held constant, as would be the case where there is prolonged rainfall or where a dam or nearby flooding requires the soil at the test site to conduct away percolating water over extensive periods.

There is, therefore, a need for apparatus and a method which provide a user with direct information on the rate at which water percolates through soil at a test location.

DISCLOSURE OF THE INVENTION

Accordingly, it is an object of this invention to provide apparatus and a method for simply and directly measuring the rate at which water percolates through soil at a test site where the subsurface water level is maintained constant on a prolonged basis at different depths below ground level.

It is a further object of this invention to provide apparatus comprising a combination of readily available and inexpensive mechanical elements for direct measurement of the rate at which water percolates through soil at a test site, especially where the subsurface water level is maintained constant on a prolonged basis at different depths below ground level.

It is a related further object of this invention to provide apparatus and methods for developing comprehensive data on soil percolation rates at different depths and locations at a test site as a function of time.

These and related objects of this invention are achieved by providing a measured supply of water through a premarked flexible hose, freely suspended in a test bore in the ground, and through a float valve assembly contained in a housing connected to the hose at its upper end and open at its lower end. Once the float valve assembly is positioned at a predetermined depth, by lowering enough hose into the test bore, the water supply is turned on. After the initial transient state, a dynamic steady-state is reached where the steady-state percolation through the soil around and below the float valve assembly, driven by the hydrostatic head of water at the level of the float valve, is equal to a measured flow rate regulated by the float valve. The water in the test bore will rise to the point where it lifts up the float within the float valve assembly towards a reducer at the end of the supply hose to throttle the flow therethrough, past the float, out the bottom of the float valve assembly, and into the test bore.

BRIEF DESCRIPTION OF THE DRAWINGS

FIG. 1 shows in partial vertical section the float valve apparatus in its inoperative state, i.e., without water present to cause the float element to be in position to be regulating water flow through the valve.

FIG. 2 shows in partial vertical section how the float valve apparatus would cooperate with a water supply to determine the soil percolation rate at a test site.

FIG. 3 shows a float and valve assembly housing in cross-section.

The same numbers are used to identify like parts or elements in each of the drawings.

BEST MODE FOR PRACTICING THE INVENTION

As indicated in FIG. 2, the apparatus of this invention is used, in part, below local ground level at a test site, where information about water percolation rates through the soil is to be determined. A vertical hole is drilled or augered into the ground, and a perforated cylindrical casing 15 is inserted therein with a small stub 25 sticking above local ground level 22.

Typically, a water supply, such as water barrel 20, is located nearby and connected through adjustable valve 19 to a flexible water supply hose 16′, which may preferably be marked along its length to facilitate determination of its other end point (the end attached to the float valve assembly) with respect to ground level 22. A water supply barrel 20 attached to hose 16' is shown equipped with a transparent sight-tube 23 which allows a user to easily see the water level 21 within. Sight tube 23 on barrel 20 may be marked in convenient units, e.g., gallons or cubic feet.

A movable clamp 7 is attached to hose 16', which, when tightened, will hold it so that a predetermined length of hose 16 is hanging vertically downward through a hole in a flat plate 18 placed above the hole casing stub 25. The rest of the apparatus, described below, is conveniently referred to as the float valve assembly and is attached to and hangs from the lower end of hose 16.

The float valve assembly, shown in detail in FIG. 1, has a cylindrical outside housing 1, with a top cover 4 and a bottom cover 2. Bottom cover 2 has at its center a large-sized hole or opening 3 to allow for exit of water flowing into housing 1 through top cover 4. Housing 1 has a smaller diameter than the inside of perforated casing 15, and so can be moved up and down freely within it. The perforations in the casing provide for continuity between the inside of the casing and the test hold wall.

The upper end of float valve assembly 1 has a female hose-to-pipe fitting 7, which attaches to male end of hose 16. A conduit nipple 6 fits onto the lower end of female hose-to-pipe fitting 7. Also threaded onto conduit nipple 6 are: a flat nut 5, a pair of flat metal conduit washers 14 which sandwich between them the top end of end 4 of cylindrical housing 1, and a pipe-to-tubing reducer 13 which has a small circular opening 12 through which water from hose 16 flows into housing 1. Opening 12 lies in a horizontal plane, in use, when housing 1 is suspended from the lower end of hose 16.

Sitting freely inside housing 1 is an essentially cylindrical float 8, which has a flat top 9 to which is preferably attached a flat flexible soft seal 10 with an upper surface 11. Float 8 is so sized and shaped as to allow free passage to water coming into housing 1 from hose 16, through the narrow annular space around it. As shown in FIG. 3, the float may preferably be made of substantially square cross-section with smooth rounded edges to ensure alignment of float 8 inside housing 1, minimizing friction between them, and ensuring an adequate throughflow area for water flow around the float and out the housing. When water initially flows through hose 16 into housing 1 it pours in through reduced opening 12 onto seal surface 11, around float 8 through the annular space between its outside and the inner cylindrical surface of housing 1. When this water reaches the lower cover of housing 1 it "floats" float 8 up and continues to flow past and out through opening 3 in bottom cover 2 of housing 1. Reference to FIG. 2 will show that this water then flows into surrounding casing 15, which at its lower end is open to the soil at a depth determined when the hole for the casing was first augered.

To commence the test operation, the float valve assembly is fitted on at the test end of hose 16 and lowered in to a predetermined point, such that movable clamp 17 attached to hose 16 rests on flat plate 18. Valve 19 is then opened to allow the flow of water, as above described, through opening 3 into casing 15. The water beings to percolate away through the soil, but if the inflow is large enough then casing 15 fills up with water all the way up to the float valve assembly. As the water level in casing 15 rises past the bottom cover 2 of housing 1 there is a simultaneous associated rise of water level around float 8 in the annular space between it and the inside of housing 1. By hydrostatic action, float 8 now floats freely upward, with water inflow through reducer opening 2 streaming past it as before, until float 8 has risen to the point where the top surface 11 of seal 10 on the float meets the rim of reducer opening 2.

Now there exists a situation of dynamic instability that is critically important to the test operation. If seal surface 11 presses upward hard enough, applying all of the available hydrostatic force, say $F_{up}$, lifting float 8 upward (i.e., not including that hydrostatic upward force needed to counter the weight of the float itself), then reducer opening 2 will be blocked, and the inflow of water shut off, when:

$F_{up}$/(area of reducer opening 12)=hydrostatic head corresponding to the distance between level of water 21 in supply barrel 20 and the plane of reducer opening 12.

This upward sealing force can be made larger by increasing the float cross-sectional area and making the reducer opening area 12 smaller. This is a factor to be taken into account in designing different elements of the float valve assembly to operate at various depths below ground level. Once the inflow of water is so shut off by the float, the level of water in casing 15 will start to drop because of percolation through the soil below and around it. As soon as the level drops so does float seal surface 11, and flow through reducer opening 12 recommences.

In practice, once a virtually steady-state flow through the soil is established, after some time, seal surface 11 will be maintained near to reducer opening 12, close enough to throttle or regulate an essentially steady flow rate therethrough. This regulated flow rate is the desired percolation rate corresponding to the particular depth at which the float valve assembly is suspended. It is related to the level 24 of subsurface water, around the casing, driving the percolation flow through the soil.

It is essential to understand that level 21 of water in the supply barrel may change extensively without significantly affecting the operation of the float valve assembly and, therefore, the accuracy of the flow rate determination. The reason is that seal surface 11 has to move up or down by only a miniscule amount, i.e., a fraction of an inch, to control the flow corresponding to changing heads above it as level 21 moves during the test. It follows that the float valve assembly very precisely holds constant the level of water in the test bore, hence in the soil, at whatever level the user chooses by raising or lowering the float valve assembly, throughout the test. This represents a significant improvement and advantage-in-use over the type of techniques hitherto employed, typified by the techniques of the Anderson and Fink patents, wherein the head of water driving the percolation mechanism varies during a test.

In practice, therefore, a user initially selects the depth of the hole made to receive casing 15, i.e., the depth of the "shallow well" into which water is to be "pumped in" to determine the "hydraulic conductivity," i.e., the percolation capability, of the soil. The user then suspends the float valve assembly at a particular depth and opens up valve 19. A short time later, float 8 begins to control the flow rate. If sight-tube 23 is marked in gallons or cubic feet the user simply notes the flow in such units per minute or hour and thus knows directly what the steady percolation rate is through the soil at that test site.

Because the apparatus is very simple and inexpensive to make, and because the holes to be drilled into the ground usually are fairly shallow and therefore also relatively inexpensive to make, it may often be possible to have an array of test bores at a given location with the testing done by a single relatively lightly skilled operator. It should be possible to use a single water supply for such an array by installing optional centrally-located flow-meters on a number of hoses leading to the different test bores. Furthermore, if automatic recording of the data is utilized, records of percolation rates can be established over prolonged periods to provide abundant data for detailed analysis, as may be desirable before locating very heavy or load-sensitive structures like nuclear power stations or runways for heavy aircraft.

It should be apparent from the preceding that the invention may be practiced otherwise than as specifically described and disclosed herein. For example, in selecting a site for underground storage of crude oil or liquid radioactive nuclear wastes, this invention may be used, as here described, with fluids other than water. Modifications may therefore be made to the specific embodiments disclosed here without departing from the scope of this invention and are intended to be included within the claims appended below:

What is claimed is:

1. An apparatus for measuring the rate of water percolation through soil, comprising:
   a supply of water;
   means for measuring the rate of flow of water drawn from said supply;
   means cooperating with said water supply for conveying said measurable flow of water to a test bore drilled into said soil at a test site to a selected depth;
   means cooperating with said conveying means for regulating said measurable flow of water into said bore, said regulating means acting in response to the level of water contained in said bore; and
   means cooperating with said conveying means for determining the location of said level of water contained in said bore with respect to a fixed reference.

2. An apparatus for measuring the rate of water percolation through soil as specified in claim 1, wherein:
   said flow regulating means is positioned inside said bore; and
   said flow regulating means contains a float whose position is responsive to said level of water in said bore; and
   said float, depending on its position, throttles said measurable flow of water through said flow regulating means into said bore.

3. An apparatus for measuring the rate of water percolation through soil as specified in claim 2, wherein:
   said flow conveying means is a flexible pipe or hose partially suspended inside said bore;
   said flow regulating means is attached to said flow conveying means at its end inside said bore so that said flow regulating means is partially submerged in water in said bore during use;
   said measurable flow is released from said conveying means through a throttlable opening inside said flow regulating means;
   said flow regulating means has an opening such that the water level surrounding said float within is the same as said level of water inside said bore during use; and
   said float carries a surface whose juxtaposition with respect to said throttlable opening throttles said measurable flow therethrough in response to said level of water in said bore.

4. An apparatus for measuring the rate of water percolation through soil as specified in claim 3, wherein:
   said float has a non-circular cross-section.

5. An apparatus for measuring the rate of water percolation through soil, as specified in claim 1, wherein:
   said means for measuring said flow rate of water is a container of water with a marked transparent portion showing the water level within, in selected units, at successive times during use.

6. An apparatus for measuring the rate of water percolation through soil, as specified in claim 1, further comprising:
   recording means, cooperating with said flow regulating means to record over time said measured rate of flow therethrough and the corresponding location of said water level in said bore with respect to a fixed reference.

7. An apparatus for measuring the rate of water percolation at a test bore drilled through soil, comprising in combination:
   a water supply barrel provided with a shut-off valve and a marked sight-tube allowing visual observation of the change in contents thereof over time;
   a flexible hose marked externally in units of length and attached at a first end to said shutoff valve to convey water therefrom into said test bore to a determinable location below ground level;
   an adjustable clamp attached to said flexible hose to determine the position of its second end with respect to a fixed reference as said second end hangs inside said test bore;
   a reducer depending from said second end of said flexible hose;
   a cylindrical housing, open at its lower end, surrounding said reducer to receive flow of water therethrough; and
   retainably contained and freely movable within said cylindrical housing, a float positioned immediately below and larger than said reducer opening to regulate water flow therethrough.

8. A method for measuring the rate of water percolation through soil, comprising the steps of:
   drilling a test bore into the ground to a selected depth;
   supplying a measurable flow of water for said percolation at said test bore;
   conveying said measurable flow of water to a determinable location inside said test bore;
   regulating said flow of water to maintain a predetermined level of water inside said test bore during a test; and
   measuring said measurable flow of water to obtain said percolation rate.

9. A method for measuring the rate of water percolation through soil as specified in claim 8, wherein:
   said regulating of said measurable flow of water is accomplished by throttling it in response to changes in said water level inside said test bore.

10. A method for measuring the rate of water percolation through soil as specified in claim 9, wherein:

said throttling to regulate said measurable flow is accomplished by the rise or fall of a float, floating inside an opening housing inside said bore so as to rise and fall with said water level inside said test bore, to partially impede said measurable flow.

11. A method for measuring the rate of water percolation through soil as specified in claim 8, comprising the further step of:

recording over time said measured flow rate of water into said test bore and the corresponding location of said level of water in said test bore.

* * * * *